US012797515B2

(12) United States Patent
Huang et al.

(10) Patent No.: US 12,797,515 B2
(45) Date of Patent: Nov. 17, 2026

(54) COMPOSITE HYDROGEL FOR LIGHT-CURED 3D CELL-LADEN PRINTING AND PREPARATION METHOD AND APPLICATION THEREOF

(71) Applicants: YANSHAN UNIVERSITY, Qinhuangdao (CN); SHANDONG UNIVERSITY, Jinan (CN)

(72) Inventors: Chuanzhen Huang, Qinhuangdao (CN); Xu Han, Shandong (CN); Hanlian Liu, Shandong (CN); Zhenyu Shi, Shandong (CN); Peng Yao, Shandong (CN); Hongtao Zhu, Shandong (CN); Bin Zou, Shandong (CN); Dun Liu, Shandong (CN); Zhen Wang, Qinhuangdao (CN); Longhua Xu, Qinhuangdao (CN); Shuiquan Huang, Qinhuangdao (CN)

(73) Assignees: YANSHAN UNIVERSITY, Qinhuangdo (CN); SHANDONG UNIVERSITY, Jinan (CN)

( * ) Notice: Subject to any disclaimer, the term of this patent is extended or adjusted under 35 U.S.C. 154(b) by 1067 days.

(21) Appl. No.: 17/939,524

(22) Filed: Sep. 7, 2022

(65) Prior Publication Data

US 2023/0405187 A1 Dec. 21, 2023

(30) Foreign Application Priority Data

Jun. 16, 2022 (CN) ........................ 202210679971.8

(51) Int. Cl.

| | |
|---|---|
| ***B33Y 10/00*** | (2015.01) |
| ***A61L 27/26*** | (2006.01) |
| ***A61L 27/52*** | (2006.01) |
| ***B33Y 40/00*** | (2020.01) |
| ***B33Y 70/00*** | (2020.01) |
| ***B33Y 80/00*** | (2015.01) |
| ***C08J 3/075*** | (2006.01) |
| ***C12N 5/00*** | (2006.01) |

(52) U.S. Cl.

CPC ............... *A61L 27/52* (2013.01); *A61L 27/26* (2013.01); *B33Y 10/00* (2014.12); *B33Y 40/00* (2014.12); *B33Y 70/00* (2014.12); *B33Y 80/00* (2014.12); *C08J 3/075* (2013.01); *C12N 5/0062* (2013.01); *C08J 2301/28* (2013.01); *C08J 2489/04* (2013.01); *C12N 2513/00* (2013.01); *C12N 2533/54* (2013.01); *C12N 2533/78* (2013.01)

(58) Field of Classification Search

None

See application file for complete search history.

(56) References Cited

U.S. PATENT DOCUMENTS

| | | | | |
|---|---|---|---|---|
| 2011/0274744 A1* | 11/2011 | Picart | ...................... | A61L 29/16 435/402 |
| 2013/0338352 A1* | 12/2013 | Yasugi | ................ | C08B 37/0072 536/55.1 |
| 2020/0123485 A1* | 4/2020 | Tamayol | ................ | C12M 33/00 |
| 2020/0179563 A1* | 6/2020 | Bagley | .................... | B29C 64/40 |
| 2024/0216581 A1* | 7/2024 | Huang | .................. | B33Y 10/00 |

OTHER PUBLICATIONS

Nguyen et al.; "The Photoinitiator Lithium Phenyl (2,4,6-Trimethylbenzoyl) Phosphinate with Exposure to 405 nm Light Is Cytotoxic to Mammalian Cells but Not Mutagenic in Bacterial Reverse Mutation Assays," 2020, MDPI, Polymers, vol. 12, 1489, pp. 1-13. (Year: 2020).*

Han et al.; "Cell-laden printed hydrogel scaffolds with glutamic acid-modified hyaluronic acid/collagen concentration gradients for directional neural stem cell migration, "2025, Elsevier, International Journal of Biological Macromolecules, vol. 322, article 146987, pp. 1-18. (Year: 2025).*

Muramatsu et al.; "Characterization of poly(L-glutamic acid)-grafted hyaluronan as a novel candidate medicine and biomedical device for intra-articular injection," 2017, Wiley; Journal of Biomedical Materials Research A, vol. 105A, Issue 11, pp. 3006-3016 (Year: 2017).*

Benjamin et al.; "Light-based 3D printing of hydrogels with high-resolution channels," 2019, IOP—Publishing; Biomedical Physics & Engineering Express, vol. 5, Article 025035, pp. 1-10. (Year: 2019).*

* cited by examiner

*Primary Examiner* — Tigabu Kassa
*Assistant Examiner* — Ivan A Greene
(74) *Attorney, Agent, or Firm* — Oliff PLC

(57) ABSTRACT

A composite hydrogel for light-cured 3D cell-laden printing and a preparation method and application thereof. The composite hydrogel of the present disclosure combines advantages of gelatin methacryloyl, sodium carboxymethylcellulose, hyaluronic acid-glutamic acid polymer, and the like. The provided composite hydrogel for 3D printing has the characteristics of low toxicity, good biocompatibility and adjustable mechanical properties, can provide cells with a three-dimensional living environment, promotes cell adhesion and migration on gradient scaffolds, and is suitable for tissue engineering scaffolds and cell-laden printing of tissues. The printing process of a scaffold is simple and can be completed within a short time, and the porosity and mechanical properties of the 3D printed hydrogel scaffold can be adjusted by adjusting the proportion of HA-Glu and Col in the hydrogel system.

8 Claims, 4 Drawing Sheets

COMPOSITE HYDROGEL FOR LIGHT-CURED 3D CELL-LADEN PRINTING AND PREPARATION METHOD AND APPLICATION THEREOF

CROSS-REFERENCES TO RELATED APPLICATIONS

This application claims priority to Chinese Patent Application No. 2022106799718, filed on 16 Jun., 2022 with the Chinese Patent Office, the disclosure of which are hereby incorporated by reference herein in its entirety.

TECHNICAL FIELD

The present disclosure relates to the technical field of biomedical materials, and in particular relates to a composite hydrogel for light-cured 3D cell-laden printing and a preparation method and application thereof.

BACKGROUND

Information of the Related Art part is merely disclosed to increase the understanding of the overall background of the present disclosure, but is not necessarily regarded as acknowledging or suggesting, in any form, that the information constitutes the prior art known to a person of ordinary skill in the art.

In tissue engineering techniques, biocompatible and biodegradable materials are used as support matrices for the delivery of cultured cells, or for three-dimensional (3D) tissue reconstruction.

Polymer hydrogels have a three-dimensional network, and can absorb and retain a large amount of water while maintaining the three-dimensional structure due to the containing of a large amount of hydrophilic groups. Due to their similarity in structure and composition to a natural extracellular matrix (ECM), hydrogels have been widely used in biological applications as well as next-generation soft, tough and biological integrated systems in wound dressings, electronics and soft machines. The polymeric network of hydrogels is usually formed through covalent interaction or noncovalent interaction. However, covalent bonds or noncovalent bonds can contribute to the strength or toughness of hydrogels. Based on the above, it is very important to develop hydrogels suitable for cell adhesion, migration and growth by adding appropriate natural materials. In addition, it is particularly important to prepare scaffolds with high precision and good biocompatibility as well as the capability of providing a carrier for three-dimensional cultured cells.

SUMMARY

To solve the problems in the prior art, the objective of the present disclosure is to provide a method for preparing a composite hydrogel and application thereof. The present disclosure prepares a composite hydrogel material for 3D bioprinting, and the composite hydrogel material has good biocompatibility, low toxicity, adjustable mechanical properties and high light-curable forming precision, can provide a carrier for three-dimensional cultured cells, and promotes cell adhesion and growth on a three-dimensional scaffold.

In order to achieve the above objective, the present disclosure adopts the technical solution:

In a first aspect, the present disclosure provides a method for preparing a composite hydrogel, which includes:

(1) grafting L-glutamic acid containing an amino group to a molecular chain of hyaluronic acid containing a carboxyl group through a peptide bond to obtain a hyaluronic acid-glutamic acid polymer (HA-Glu), the polymer introduces relevant properties of glutamic acid while retaining the original properties of hyaluronic acid and provides a favorable living environment for nerve cells; dissolving the hyaluronic acid-glutamic acid polymer (HA-Glu), type I collagen (Col) and sodium chloride (NaCl) in an HCl solution to form a mixed solution of the hyaluronic acid-glutamic acid polymer and the collagen (HA-Glu/Col mixed solution);

(2) dissolving a photoinitiator lithium phenyl-2,4,6-trimethylbenzoylpho-sphinate (LAP) in an NaCl solution and heating a resulting solution in a water bath to form an LAP solution;

(3) dissolving gelatin methacryloyl (GelMA) in the LAP solution, and heating a resulting solution in a water bath until the gelatin methacryloyl fully dissolves to form a gelatin methacryloyl solution;

(4) dissolving sodium carboxymethyl cellulose (NaCMC) in the LAP solution, and heating a resulting solution in a water bath until the sodium carboxymethyl cellulose fully dissolves to form a sodium carboxymethyl cellulose solution; and (5) mixing the HA-Glu/Col mixed solution prepared in step (1), the gelatin methacryloyl solution prepared in step (3) and the sodium carboxymethyl cellulose solution prepared in step (4), respectively, then adding a tartrazine with light-blocking property, and performing sterile filtration with a 0.22 μm sterile filter to finally obtain the composite hydrogel.

Further, a method for preparing the hyaluronic acid-glutamic acid polymer specifically includes: in step (1), dissolving hyaluronic acid in an MES buffer at 55 °C, and then adding 1-ethyl-3-(3-dimethylaminopropyl) carbodiimide hydrochloride (EDC) and N-hydroxysuccinimide (NHS) to the solution for activation at 37 °C; and after the activation, dissolving L-glutamic acid hydrochloride in the solution at 37 °C, and continuing to stir the solution at 37 °C for sufficient reaction. Preferably, mass volume concentrations g/mL of the hyaluronic acid, the 1-ethyl-3-(3-dimethylaminopropyl) carbodiimide hydrochloride, the N-hydroxysuccinimide and the L-glutamic acid hydrochloride in the solution system are 1 (w/v) %, 0.72 (w/v) %, 0.44 (w/v) % and 1.46 (w/v) %, respectively.

Further, the collagen is dissolved in the HCl solution at 4 °C, then sodium chloride is added, the solution is heated to 37 °C, and the hyaluronic acid-glutamic acid polymer is added to the solution and stirred to fully dissolve; and the pH is adjusted with 0.1 M NaOH at 37 °C to finally obtain the mixed solution of the hyaluronic acid-glutamic acid polymer and the collagen.

A total mass volume concentration of the hyaluronic acid-glutamic acid polymer to the collagen as a solute in the solution is 2%, and a mass ratio of the hyaluronic acid-glutamic acid polymer to the collagen is 1:7-7:1, and more preferably, 1:1.

Further, in step (2), a mass volume concentration of the photoinitiator lithium phenyl-2,4,6-trimethylbenzoylphosphinate in the LAP solution is 0.25%.

Further, in step (2), heating is performed in the water bath at 60 °C for 30 min.

Further, in step (3), a mass volume concentration of the gelatin methacryloyl solution is 14%.

Further, in step (3), heating is performed in the water bath at 60 °C.

Further, in step (4), a mass volume concentration of the sodium carboxymethyl cellulose solution is 1.9%.

Further, in step (4), heating is performed in the water bath at 60 °C.

Further, in step (5), a volume fraction of the gelatin methacryloyl solution in the composite solution is 42% (v/v).

Further, in step (5), a volume fraction of the sodium carboxymethyl cellulose solution in the composite solution is 16% (v/v).

Further, in step (5), a volume fraction of the mixed solution of the hyaluronic acid-glutamic acid polymer and the collagen in the composite solution is 42% (v/v).

Further, in step (5), a concentration of the tartrazine with light-blocking property in the composite solution is 0.05% (w/v).

In a second aspect, the present disclosure provides a composite hydrogel for light-cured 3D cell-laden printing prepared by the above method.

In a third aspect, the present disclosure further provides a method for preparing a composite hydrogel scaffold from the above composite hydrogel, which includes:

- in a sterile environment, uniformly mixing the composite hydrogel with mouse NE-4C neural stem cells, and then performing light-cured 3D printing under 405-nm ultraviolet light to obtain the composite hydrogel scaffold.

Further, in a light-cured 3D printer, a deposition platform is at a temperature of 29 °C, and a material tank is at a temperature of 29 °C.

Further, a single-layer thickness is 100 μm, a light intensity is 15 $mW/cm^2$, a number of basic layers is 5, an exposure time of basic layers is 20 s, and an exposure time of sheet layers is 20 s.

Further, a Z-axis speed is 25 mm/min, a stripping distance is 6 mm, a stripping speed is 25 mm/min, and a stripping recovery speed is 100 mm/min.

In a fourth aspect, the present disclosure further provides a composite hydrogel scaffold prepared by the above method.

By the method of the present disclosure, the hyaluronic acid with the carboxyl group is connected with the glutamic acid with the amino group under the activation of EDC and NHS to form the hyaluronic acid-glutamic acid polymer, which not only retains the original chemical properties of hyaluronic acid, but also introduces relevant properties of glutamic acid to provide a favorable living environment for nerve cells. Under the irradiation of the 405-nm ultraviolet light, an initiator absorbs light energy and generates free radicals, and the GelMA monomer and the free radicals undergo a chain growth reaction, that is, GelMA molecules form a covalent bond and generate a polymerization network, thereby forming a GelMA polymer network with good formability. The amino groups, hydroxyl groups and carboxyl groups of the sodium carboxymethylcellulose, the collagen and the hyaluronic acid-glutamic acid polymer in the scaffold form hydrogen bonds, and help the network in the scaffold to be dynamically stable, thereby improving the structural stability of the scaffold.

The present disclosure has the following beneficial effects:

(1) Cell-laden printing of a hydrogel scaffold can be realized by the light-cured 3D bioprinting technology, and the scaffold has controllable morphology, good formability, high precision and good stability.

(2) As a light-sensitive material, the added GelMA can construct a hydrogel scaffold through light-curing. The hydrogel scaffold contains RGD polypeptide to stimulate cell growth and differentiation, provides adhesion sites for cells, and has excellent biocompatibility. The added NaCMC can increase the mechanical properties of the hydrogel scaffold and ensure that the cured hydrogel keeps stable. The prepared hyaluronic acid-glutamic acid polymer not only retains the original chemical properties of hyaluronic acid, can resist tissue compression and cell damage, and acts as a damper; but also introduces the relevant properties of glutamic acid, can be used as a tonic for the nerve center and cerebral cortex, has a certain effect on the treatment of nerve damage, and can provide a favorable living environment for nerve cells. The added collagen is one of the main components of the extracellular matrix and has excellent low immunogenicity. The composite hydrogel has the comprehensive properties of excellent biocompatibility, rapid gelation and good formability, and provides a new light-cured material for tissue engineering.

(3) The printing process of the scaffold is simple and can be completed within a short time, and the porosity and mechanical properties of the 3D printed hydrogel scaffold can be adjusted by adjusting the proportion of HA-Glu and Col in the hydrogel system.

BRIEF DESCRIPTION OF THE DRAWINGS

The accompanying drawings constituting a part of the present disclosure are used for providing further understanding for the present disclosure. Exemplary embodiments of the present disclosure and descriptions thereof are used for explaining the present disclosure and do not constitute any inappropriate limitation to the present disclosure.

FIG. 2(*b*) is a hydrogen nuclear magnetic resonance spectrum of the hyaluronic acid-glutamic acid polymers prepared in Examples 1 to 5 of the present disclosure.

FIG. 3(*a*) shows a GM/CMC/1HA-Glu/7Col hydrogel prepared in Example 1; FIG. 3(*b*) shows a GM/CMC/2HA-Glu/6Col hydrogel prepared in Example 2; FIG. 3(*c*) shows a GM/CMC/4HA-Glu/4Col hydrogel prepared in Example 3; FIG. 3(*d*) shows a GM/CMC/6HA-Glu/2Col hydrogel prepared in Example 4; and FIG. 3(*e*) shows a GM/CMC/7HA-Glu/1Col hydrogel prepared in Example 5.

FIG. 6(*a*) is a curve diagram showing variation of storage modulus G' and loss modulus G" of the hydrogels along with strain, and FIG. 6(*b*) is a curve diagram showing gel kinetics of the hydrogels.

DETAILED DESCRIPTION

Figure 1:
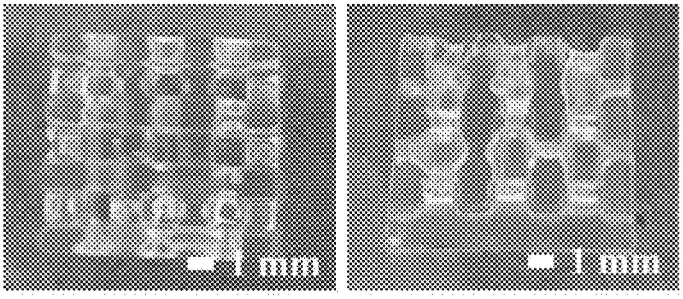
FIG. 1 is a diagram of a light-cured 3D printing scaffold of Example 3 of the present disclosure.

It should be noted that, the following detailed descriptions are all exemplary, and are intended to provide further descriptions of the present disclosure. Unless otherwise specified, all technical and scientific terms used in the present disclosure have the same meanings as those usually understood by a person of ordinary skill in the art to which the present disclosure belongs.

The technical solutions and implementation process of the present disclosure are described in detail in conjunction with the following embodiments and accompanying drawings. The following embodiments are intended to illustrate the present disclosure and do not limit the scope thereof.

As some embodiments of the present disclosure, a method for preparing a composite hydrogel for light-cured 3D cell-laden printing and a scaffold with the same include the following raw materials: 42% (v/v) of a GelMA solution with a concentration of 14% (w/v) in the composite solution; 16% (v/v) of an NaCMC solution with a concentration of 1.9% (w/v) in the composite solution; and 42% (v/v) of a mixed solution of HA-Glu and Col (HA-Glu/Col mixed solution) in the composite solution, where a concentration of HA-Glu/Col as a solute is 2% (w/v), a mass ratio of HA-Glu to Col is 1:7, 2:6, 4:4, 6:2 and 7:1 respectively, and a concentration of LAP in the composite solution is 0.145% (w/v).

Example 1

(1) Preparation of a hyaluronic acid-glutamic acid polymer (HA-Glu): 1 g of hyaluronic acid was dissolved in 100 ml of MES buffer (50 mM, ph 4.7), and the solution was heated in a water bath to 55 °C for 30 min with shaking 3 times. Then heating was stopped. When the solution temperature reached 37 °C, 0.72 g of 1-ethyl-3-(3-dimethylaminopropyl) carbodiimide hydrochloride (EDC) and 0.44 g of N-hydroxysuccinimide (NHS) were respectively added to the solution for activation for 15-20 min. After the activation, 1.46 g of L-glutamic acid hydrochloride was dissolved in the above solution at 37 °C, and the solution was continued to be stirred at 37 °C for 24 h for sufficient reaction. After the reaction, the mixture was transferred to a dialysis bag with a molecular weight of 12000, dialyzed in a 0.1 M NaCl aqueous solution for 12 h firstly, and then dialyzed in deionized water for 8 days, during which the deionized water was replaced every day. After the dialysis, the solution was centrifuged in a centrifuge at 5750 r/min for 5 min. Then, the solution was placed in a rotary evaporator for rotary concentration. After the concentration, the solution was aliquoted and transferred to an ultra-low temperature refrigerator for freezing for 2 h. Then, the frozen material was transferred to a freeze drier without thawing for freeze-drying until the material was completely dehydrated (for about 2-3 days). Finally, the freeze-dried material was sealed in a bottle and refrigerated for later use.

(2) Preparation of a mixed solution of the hyaluronic acid-glutamic acid polymer (HA-Glu) and type I collagen (Col): 0.35 g of collagen (Col) was dissolved in 20 ml of 0.01 M HCl solution, the solution was cooled in a water bath to 4 °C and continuously stirred for 15 min, and then 0.468 g of sodium chloride was added to the solution and continuously stirred for 5 min. The solution was then heated to 37 °C, and 0.05 g of the hyaluronic acid-glutamic acid polymer (HA-Glu) was added to the solution and stirred to fully dissolve. After dissolution, the pH was adjusted to 5 with 0.1 M NaOH at 37 °C. Finally, a mixed solution of HA-Glu and Col (HA-Glu/Col mixed solution) was obtained, where a concentration of HA-Glu/Col as a solute was 2% (w/v), and a mass ratio of HA-Glu to Col was 1:7, that was, a 1HA-Glu/7Col mixed solution was obtained.

(3) Preparation of an LAP solution: 0.1 g of a photoinitiator lithium phenyl-2,4,6-trimethylbenzoylpho-sphinate (LAP) was dissolved in 40 ml of 0.4 M NaCl solution, and the solution was heated in a water bath to 60 °C for 30 min with shaking 3 times to form an LAP solution with a concentration of 0.25% (w/v).

(4) Preparation of a gelatin methacryloyl (GelMA) solution: 1.4 g of GelMA was dissolved in 10 ml of LAP solution, and the solution was continuously heated in a water bath at 60 °C with shaking 3 times to fully dissolve the GelMA to form a GelMA solution with a concentration of 14% (w/v).

(5) Preparation of a sodium carboxymethyl cellulose (NaCMC) solution: 0.19 g of NaCMC was dissolved in 10 ml of LAP solution, and the solution was continuously heated in a water bath at 60 °C with shaking 3 times to fully dissolve the NaCMC to form an NaCMC solution with a concentration of 1.9% (w/v).

(6) Preparation of a composite solution: 4.2 ml of GelMA solution, 1.6 ml of NaCMC solution and 4.2 ml of 1HA-Glu/7Col mixed solution were respectively added to a container and stirred evenly, and then 0.005 g of a tartrazine with light-blocking property was added, during this period, the solution was continuously heated in a water bath at 37 °C with shaking 3 times. Finally, sterile filtration was performed with a 0.22 μm sterile filter to form 10 ml of composite solution, which was denoted as GM/CMC/1HA-Glu/7Col.

(7) DLP light-cured 3D printing of the prepared composite solution to obtain a hydrogel scaffold: in a sterile environment, the composite solution was evenly mixed with mouse NE-4C neural stem cells, and a usage ratio of the composite solution to the mouse NE-4C neural stem cells was 1 mL:$1\times10^6$. Light-cured 3D printing was performed using a DLP printer to form a scaffold. In the light-cured 3D printer, a deposition platform was at a temperature of 29 °C, a material tank was at a temperature of 29 °C, a single-layer thickness was 100 μm, a light intensity was 15 $mW/cm^2$, a number of basic layers was 5, an exposure time of basic layers was 20 s, an exposure time of sheet layers was 20 s, a Z-axis speed was 25 mm/min, a stripping distance was 6 mm, a stripping speed was 25 mm/min, and a stripping recovery speed was 100 mm/min.

Example 2

(1) Preparation of a hyaluronic acid-glutamic acid polymer (HA-Glu): same as that in Example 1.

(2) Preparation of a mixed solution of the hyaluronic acid-glutamic acid polymer (HA-Glu) and type I collagen (Col): 0.3 g of collagen (Col) was dissolved in 20 ml of 0.01 M HCl solution, the solution was cooled in a water bath to 4 °C and continuously stirred for 15 min, and then 0.468 g of sodium chloride was added to the solution and continuously stirred for 5 min. The solution was then heated to 37 °C, and 0.1 g of the hyaluronic acid-glutamic acid polymer (HA-Glu) was added to the solution and stirred to fully dissolve. After dissolution, the pH was adjusted to 5 with 0.1 M NaOH at 37 °C. Finally, a mixed solution of HA-Glu and Col (HA-Glu/Col mixed solution) was obtained, where a concentration of HA-Glu/Col as a solute was 2% (w/v), and a mass ratio of HA-Glu to Col was 2:6, that was, a 2HA-Glu/6Col mixed solution was obtained.

(3) Preparation of an LAP solution: 0.1 g of a photoinitiator lithium phenyl-2,4,6-trimethylbenzoylpho-sphinate (LAP) was dissolved in 40 ml of 0.4 M NaCl solution, and the solution was heated in a water bath to 60 °C for 30 min with shaking 3 times to form an LAP solution with a concentration of 0.25% (w/v).

(4) Preparation of a gelatin methacryloyl (GelMA) solution: 1.4 g of GelMA was dissolved in 10 ml of LAP solution, and the solution was continuously heated in a water bath at 60 °C with shaking 3 times to fully dissolve the GelMA to form a GelMA solution with a concentration of 14% (w/v).

(5) Preparation of a sodium carboxymethyl cellulose (NaCMC) solution: 0.19 g of NaCMC was dissolved in 10 ml of LAP solution, and the solution was continuously heated in a water bath at 60 °C with shaking 3 times to fully dissolve the NaCMC to form an NaCMC solution with a concentration of 1.9% (w/v).

(6) Preparation of a composite solution: 4.2 ml of GelMA solution, 1.6 ml of NaCMC solution and 4.2 ml of 2HA-Glu/6Col mixed solution were respectively added to a container and stirred evenly, and then 0.005 g of a tartrazine with light-blocking property was added, during this period, the solution was continuously heated in a water bath at 37 °C with shaking 3 times. Finally, sterile filtration was performed with a 0.22 μm sterile filter to form 10 ml of composite solution, which was denoted as GM/CMC/2HA-Glu/6Col.

(7) DLP light-cured 3D printing of the prepared composite solution to obtain a hydrogel scaffold: in a sterile environment, the composite solution was evenly mixed with mouse NE-4C neural stem cells, and a usage ratio of the composite solution to the mouse NE-4C neural stem cells was 1 mL:$1\times10^6$. Light-cured 3D printing was performed using a DLP printer to form a scaffold. In the light-cured 3D printer, a deposition platform was at a temperature of 29 °C, a material tank was at a temperature of 29 °C, a single-layer thickness was 100 μm, a light intensity was 15 mW/cm$^2$, a number of basic layers was 5, an exposure time of basic layers was 20 s, an exposure time of sheet layers was 20 s, a Z-axis speed was 25 mm/min, a stripping distance was 6 mm, a stripping speed was 25 mm/min, and a stripping recovery speed was 100 mm/min.

Example 3

(1) Preparation of a hyaluronic acid-glutamic acid polymer (HA-Glu): same as that in Example 1.

(2) Preparation of a mixed solution of the hyaluronic acid-glutamic acid polymer (HA-Glu) and type I collagen (Col): 0.2 g of collagen (Col) was dissolved in 20 ml of 0.01 M HCl solution, the solution was cooled in a water bath to 4 °C and continuously stirred for 15 min, and then 0.468 g of sodium chloride was added to the solution and continuously stirred for 5 min. The solution was then heated to 37 °C, and 0.2 g of the hyaluronic acid-glutamic acid polymer (HA-Glu) was added to the solution and stirred to fully dissolve. After dissolution, the pH was adjusted to 5 with 0.1 M NaOH at 37 °C. Finally, a mixed solution of HA-Glu and Col (HA-Glu/Col mixed solution) was obtained, where a concentration of HA-Glu/Col as a solute was 2% (w/v), and a mass ratio of HA-Glu to Col was 4:4, that was, a 4HA-Glu/4Col mixed solution was obtained.

(3) Preparation of an LAP solution: 0.1 g of a photoinitiator lithium phenyl-2,4,6-trimethylbenzoylpho-sphinate (LAP) was dissolved in 40 ml of 0.4 M NaCl solution, and the solution was heated in a water bath to 60 °C for 30 min with shaking 3 times to form an LAP solution with a concentration of 0.25% (w/v).

(4) Preparation of a gelatin methacryloyl (GelMA) solution: 1.4 g of GelMA was dissolved in 10 ml of LAP solution, and the solution was continuously heated in a water bath at 60 °C with shaking 3 times to fully dissolve the GelMA to form a GelMA solution with a concentration of 14% (w/v).

(5) Preparation of a sodium carboxymethyl cellulose (NaCMC) solution: 0.19 g of NaCMC was dissolved in 10 ml of LAP solution, and the solution was continuously heated in a water bath at 60 °C with shaking 3 times to fully dissolve the NaCMC to form an NaCMC solution with a concentration of 1.9% (w/v).

(6) Preparation of a composite solution: 4.2 ml of GelMA solution, 1.6 ml of NaCMC solution and 4.2 ml of 4HA-Glu/4Col mixed solution were respectively added to a container and stirred evenly, and then 0.005 g of a tartrazine with light-blocking property was added, during this period, the solution was continuously heated in a water bath at 37 °C with shaking 3 times. Finally, sterile filtration was performed with a 0.22 μm sterile filter to form 10 ml of composite solution, which was denoted as GM/CMC/4HA-Glu/4Col.

(7) DLP light-cured 3D printing of the prepared composite solution to obtain a hydrogel scaffold: in a sterile environment, the composite solution was evenly mixed with mouse NE-4C neural stem cells, and a usage ratio of the composite solution to the mouse NE-4C neural stem cells was 1 mL:$1\times10^6$. Light-cured 3D printing was performed using a DLP printer to form a scaffold. In the light-cured 3D printer, a deposition platform was at a temperature of 29 °C, a material tank was at a temperature of 29 °C, a single-layer thickness was 100 μm, a light intensity was 15 mW/cm$^2$, a number of basic layers was 5, an exposure time of basic layers was 20 s, an exposure time of sheet layers was 20 s, a Z-axis speed was 25 mm/min, a stripping distance was 6 mm, a stripping speed was 25 mm/min, and a stripping recovery speed was 100 mm/min.

Example 4

(1) Preparation of a hyaluronic acid-glutamic acid polymer (HA-Glu): same as that in Example 1.

(2) Preparation of a mixed solution of the hyaluronic acid-glutamic acid polymer (HA-Glu) and type I collagen (Col): 0.1 g of collagen (Col) was dissolved in 20 ml of 0.01 M HCl solution, the solution was cooled in a water bath to 4 °C and continuously stirred for 15 min, and then 0.468 g of sodium chloride was added to the solution and continuously stirred for 5 min. The solution was then heated to 37 °C, and 0.3 g of the hyaluronic acid-glutamic acid polymer (HA-Glu) was added to the solution and stirred to fully dissolve. After dissolution, the pH was adjusted to 5 with 0.1 M NaOH at 37 °C. Finally, a mixed solution of HA-Glu and Col (HA-Glu/Col mixed solution) was obtained, where a concentration of HA-Glu/Col as a solute was 2% (w/v), and a mass ratio of HA-Glu to Col was 6:2, that was, a 6HA-Glu/2Col mixed solution was obtained.

(3) Preparation of an LAP solution: 0.1 g of a photoinitiator lithium phenyl-2,4,6-trimethylbenzoylpho-sphinate (LAP) was dissolved in 40 ml of 0.4 M NaCl solution, and the solution was heated in a water bath to 60 °C for 30 min with shaking 3 times to form an LAP solution with a concentration of 0.25% (w/v).

(4) Preparation of a gelatin methacryloyl (GelMA) solution: 1.4 g of GelMA was dissolved in 10 ml of LAP solution, and the solution was continuously heated in a water bath at 60 °C with shaking 3 times to fully dissolve the GelMA to form a GelMA solution with a concentration of 14% (w/v).

(5) Preparation of a sodium carboxymethyl cellulose (NaCMC) solution: 0.19 g of NaCMC was dissolved in 10 ml of LAP solution, and the solution was continuously heated in a water bath at 60 °C with shaking 3 times to fully dissolve the NaCMC to form an NaCMC solution with a concentration of 1.9% (w/v).

(6) Preparation of a composite solution: 4.2 ml of GelMA solution, 1.6 ml of NaCMC solution and 4.2 ml of 6HA-Glu/2Col mixed solution were respectively added to a container and stirred evenly, and then 0.005 g of a tartrazine with light-blocking property was added, during this period, the solution was continuously heated in a water bath at 37 °C with shaking 3 times. Finally, sterile filtration was performed with a 0.22 μm sterile filter to form 10 ml of composite solution, which was denoted as GM/CMC/6HA-Glu/2Col.

(7) DLP light-cured 3D printing of the prepared composite solution to obtain a hydrogel scaffold: in a sterile environment, the composite solution was evenly mixed with mouse NE-4C neural stem cells, and a usage ratio of the composite solution to the mouse NE-4C neural stem cells was 1 mL:$1\times10^6$. Light-cured 3D printing was performed using a DLP printer to form a scaffold. In the light-cured 3D printer, a deposition platform was at a temperature of 29 °C, a material tank was at a temperature of 29 °C, a single-layer thickness was 100 μm, a light intensity was 15 mW/$cm^2$, a number of basic layers was 5, an exposure time of basic layers was 20 s, an exposure time of sheet layers was 20 s, a Z-axis speed was 25 mm/min, a stripping distance was 6 mm, a stripping speed was 25 mm/min, and a stripping recovery speed was 100 mm/min.

Example 5

(1) Preparation of a hyaluronic acid-glutamic acid polymer (HA-Glu): same as that in Example 1.

(2) Preparation of a mixed solution of the hyaluronic acid-glutamic acid polymer (HA-Glu) and type I collagen (Col): 0.05 g of collagen (Col) was dissolved in 20 ml of 0.01 M HCl solution, the solution was cooled in a water bath to 4 °C and continuously stirred for 15 min, and then 0.468 g of sodium chloride was added to the solution and continuously stirred for 5 min. The solution was then heated to 37 °C, and 0.35 g of the hyaluronic acid-glutamic acid polymer (HA-Glu) was added to the solution and stirred to fully dissolve. After dissolution, the pH was adjusted to 5 with 0.1 M NaOH at 37 °C. Finally, a mixed solution of HA-Glu and Col (HA-Glu/Col mixed solution) was obtained, where a concentration of HA-Glu/Col as a solute was 2% (w/v), and a mass ratio of HA-Glu to Col was 7:1, that was, a 7HA-Glu/1Col mixed solution was obtained.

(3) Preparation of an LAP solution: 0.1 g of a photoinitiator lithium phenyl-2,4,6-trimethylbenzoylpho-sphinate (LAP) was dissolved in 40 ml of 0.4 M NaCl solution, and the solution was heated in a water bath to 60 °C for 30 min with shaking 3 times to form an LAP solution with a concentration of 0.25% (w/v).

(4) Preparation of a gelatin methacryloyl (GelMA) solution: 1.4 g of GelMA was dissolved in 10 ml of LAP solution, and the solution was continuously heated in a water bath at 60 °C with shaking 3 times to fully dissolve the GelMA to form a GelMA solution with a concentration of 14% (w/v).

(5) Preparation of a sodium carboxymethyl cellulose (NaCMC) solution: 0.19 g of NaCMC was dissolved in 10 ml of LAP solution, and the solution was continuously heated in a water bath at 60 °C with shaking 3 times to fully dissolve the NaCMC to form an NaCMC solution with a concentration of 1.9% (w/v).

(6) Preparation of a composite solution: 4.2 ml of GelMA solution, 1.6 ml of NaCMC solution and 4.2 ml of 7HA-Glu/1Col mixed solution were respectively added to a container and stirred evenly, and then 0.005 g of a tartrazine with light-blocking property was added, during this period, the solution was continuously heated in a water bath at 37 °C with shaking 3 times. Finally, sterile filtration was performed with a 0.22 μm sterile filter to form 10 ml of composite solution, which was denoted as GM/CMC/7HA-Glu/1Col.

(7) DLP light-cured 3D printing of the prepared composite solution to obtain a hydrogel scaffold: in a sterile environment, the composite solution was evenly mixed with mouse NE-4C neural stem cells, and a usage ratio of the composite solution to the mouse NE-4C neural stem cells was 1 mL:$1\times10^6$. Light-cured 3D printing was performed using a DLP printer to form a scaffold. In the light-cured 3D printer, a deposition platform was at a temperature of 29 °C, a material tank was at a temperature of 29 °C, a single-layer thickness was 100 μm, a light intensity was 15 mW/$cm^2$, a number of basic layers was 5, an exposure time of basic layers was 20 s, an exposure time of sheet layers was 20 s, a Z-axis speed was 25 mm/min, a stripping distance was 6 mm, a stripping speed was 25 mm/min, and a stripping recovery speed was 100 mm/min.

In the following, the advantages of the hydrogel materials of the Examples applied to tissue engineering scaffolds or cell-laden printed tissues are illustrated through the following tests.

Formability characterization: a 3D printed porous scaffold of the hydrogel material of Example 3 is shown in FIG. 1, from which it can be found that the hydrogel scaffold has a porous morphology, no swelling or damage, no blockage or collapse, and a relatively stable structure.

Figure 2:
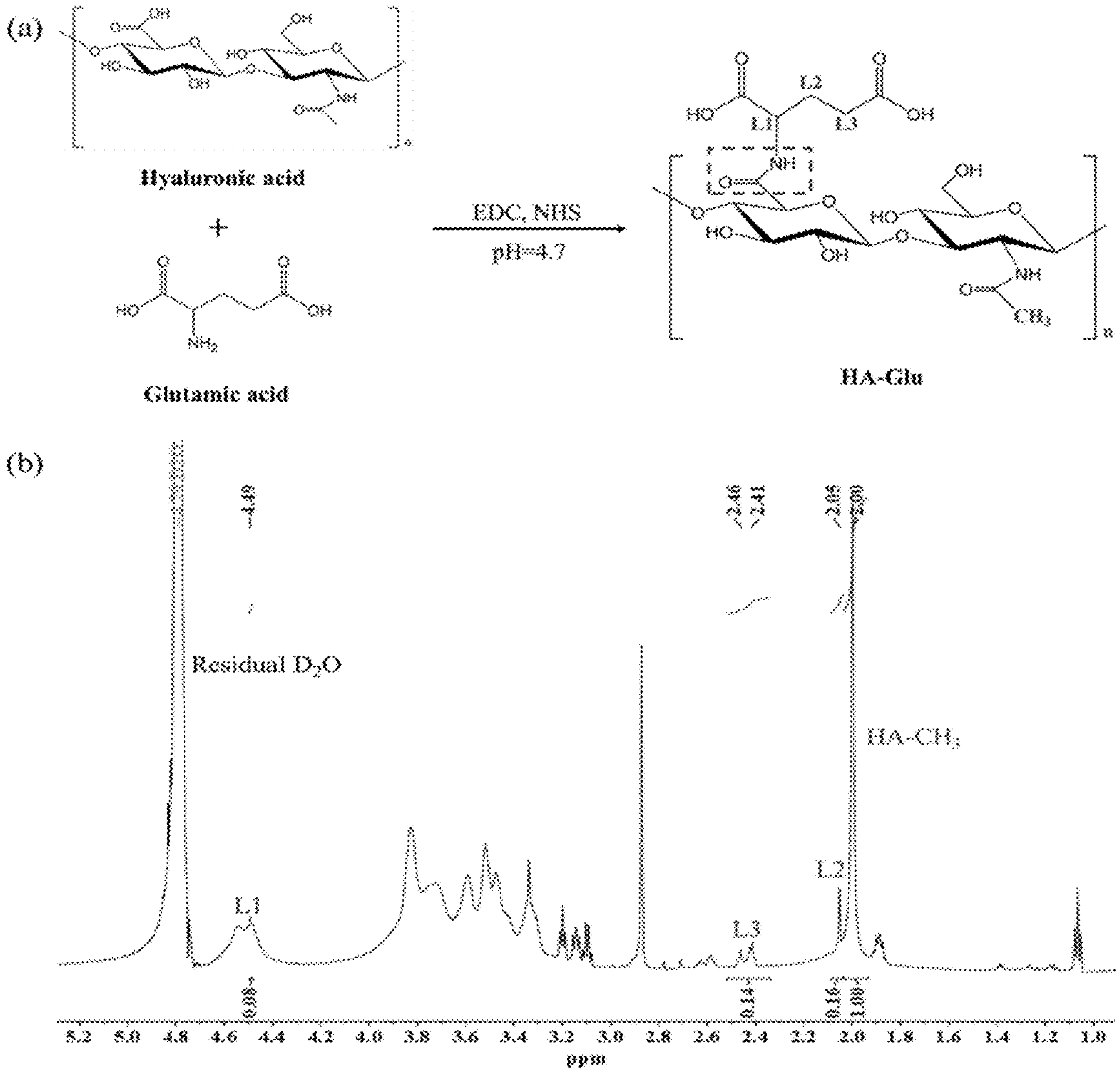
FIG. 2(*a*) is a schematic diagram of hyaluronic acid-glutamic acid polymers prepared in Examples 1 to 5 of the present disclosure.

Analysis of a new material HA-Glu: the principle of preparing the new HA-Glu materials of Examples 1 to 5 is shown in FIG. 2(*a*). Hyaluronic acid with a carboxyl group and glutamic acid with an amino group react in the presence of activators EDC and NHS, and finally the carboxyl group and the amino group react to form a peptide bond, and glutamic acid is grafted onto hyaluronic acid. The hydrogen nuclear magnetic resonance spectrum of the new HA-Glu materials prepared in Examples 1 to 5 is shown in FIG. 2(*b*). From the hydrogen spectrum, it can be found that the peak at 4.79 ppm is characterized by D2O, the peak at 2.00 ppm is characterized by methyl-$CH_3$ on the HA chain, and L1, L2, and L3 correspond to three hydrocarbon groups on glutamic acid respectively. The graft ratio of Glu to HA is calculated by an equation as follows:

$$DS = \frac{\int L2}{\int HA - CH_3} \times \frac{3}{2} \times 100\% = 24\%$$

It can be seen that Glu has been successfully grafted onto HA.

Figure 3:
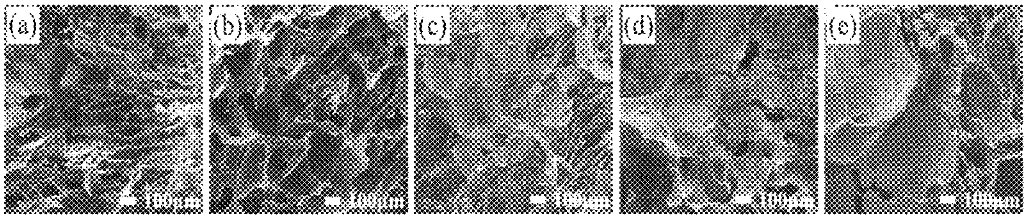
FIG. 3 is a micro morphology diagram of hydrogels prepared in Examples 1 to 5 of the present disclosure under a scanning electron microscope.

Micro morphology characterization of a hydrogel: the hydrogel materials of Example 1, Example 2, Example 3, Example 4 and Example 5 are respectively light-cured, freeze-dried, sprayed with gold, and investigated the internal polymer network by field emission scanning electron microscopy (JEOL, JSM-7610F) at an AC accelerating voltage of 5 kv, as shown in FIG. 3. From the electron microscope images, it can be seen that all the hydrogel materials have a porous structure inside. When the Col content is higher, the pore size is smaller, the pore wall is thinner, and the truncated surface is fibrous. When the HA-Glu content increases, the pore size increases, the wall thickness increases, the porosity increases, and a change from a fibrous structure to a flaky structure can be observed. Therefore, by changing the ratio of HA-Glu to Col, the microstructure of the composite hydrogel can be changed.

Characterization of swelling property: the hydrogel materials of Example 1, Example 2, Example 3, Example 4 and Example 5 are respectively light-cured and freeze-dried, and then prepared into small cylinders with a diameter of 9 mm and a height of 5 mm. The cylindrical samples of the hydrogels are then freeze-dried and weighed ($W_0$), and soaked in PBS solutions at 37 °C to swell with water. Then, the samples are taken out at different time points after incubation for 10 min, 30 min, 1 h, 2 h, 6 h, 12 h, 24 h, 36 h, 48 h, 72 h and 96 h respectively, and then the samples with surface moisture being removed are weighed ($W_n$) respectively. The swelling rate can be calculated using an equation (1) as follows:

$$W_{ratio}=(W_n-W_0)/W_0\times100\%$$

Figure 4:
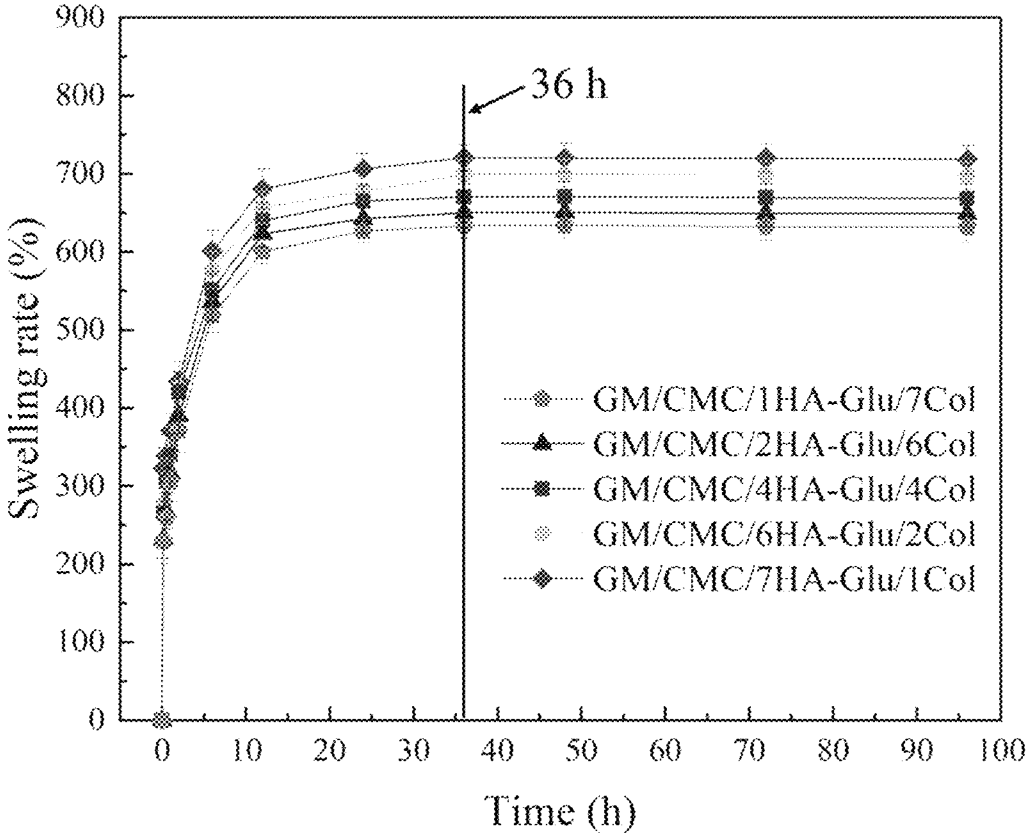
FIG. 4 is a diagram showing swelling of hydrogels prepared in Examples 1 to 5 of the present disclosure.

The swelling rates of the hydrogels of different compositions are shown in FIG. 4, from which it can be found that the swelling rates of the GM/CMC/1HA-Glu/7Col, GM/CMC/2HA-Glu/6Col, GM/CMC/4HA-Glu/4Col, GM/CMC/6HA-Glu/2Col and GM/CMC/7HA-Glu/1Col hydrogels are 633%, 650%, 670%, 699% and 720% respectively. With the increase of the HA-Glu content, the water absorption capacity of the hydrogel is improved. This is because that there is a large amount of carboxyl groups-$COO^-$on the main chain of HA in HA-Glu, and there are also some carboxyl groups in the grafted Glu. Therefore, the increase of hydrophilic groups improves the water absorption capacity.

Figure 5:
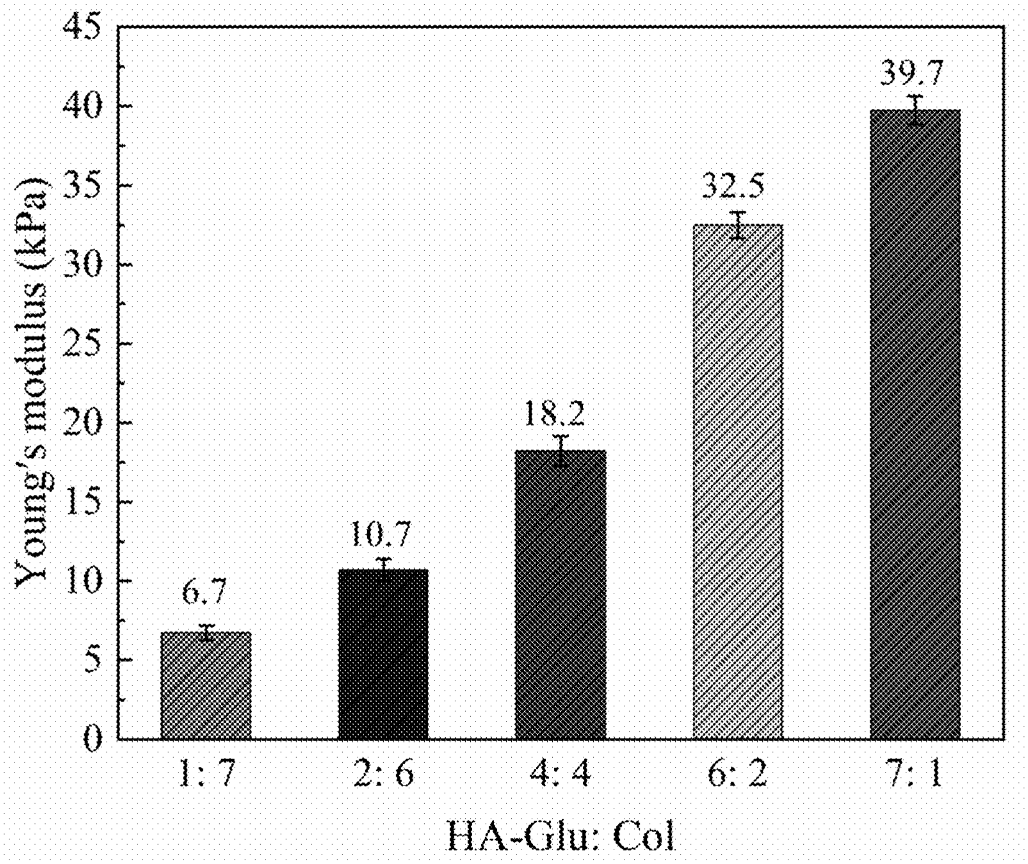
FIG. 5 is a diagram showing compressive modulus of hydrogels prepared in Examples 1 to 5 of the present disclosure.

Mechanical property characterization: the mechanical properties of the hydrogels of Examples 1 to 5 are characterized using a universal testing machine (ZLC-2D, Jinan XLC Testing Machine Co., Ltd.) in air at a loading rate of 2 mm/min and a 100 N load cell, as shown in FIG. 5. With the increase of the HA-Glu content, the Young's modulus of the hydrogel gradually increases, the hardness of the hydrogel gradually increases, and the modulus is within a range of 6.7 kPa-39.7 kPa. Therefore, by changing the ratio of HA-Glu to Col, the Young's modulus of the composite hydrogel can be changed and adjusted.

Figure 6:
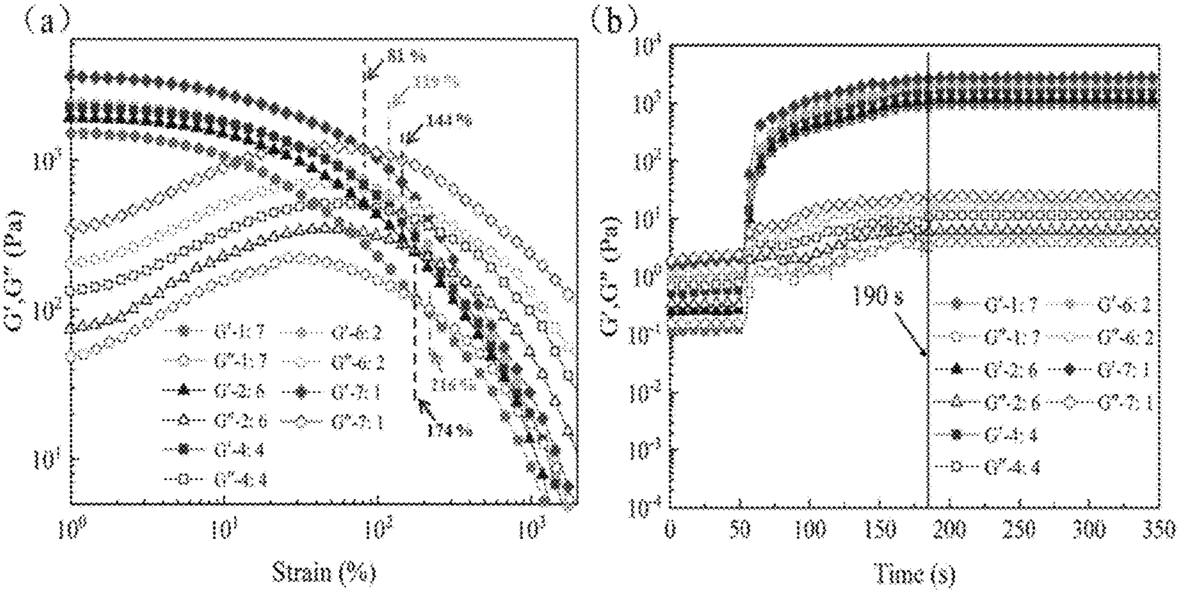
FIG. 6 is a diagram showing rheological properties of hydrogels prepared in Examples 1 to 5 of the present disclosure.

Rheological property characterization: rheological analysis of the hydrogels of Examples 1 to 5 is performed at room temperature using Anton Paar MCr 302 and 1° cone and plate. During the experiment, to prevent water loss, the edge of the plate is sealed with silicone oil. FIG. 6(*a*) shows the storage modulus (G') and loss modulus (G") of the cured hydrogel as a function of strain. At a small strain, it can be seen that the higher the HA-Glu content, the greater the G', and the harder the cured hydrogel. The higher the HA-Glu content, the smaller the strain value at the intersection of the G' and G" curves, and the more likely it is for the cured hydrogel to break under the same strain condition. FIG. 6(*b*) shows the gel kinetic curves of the hydrogels of Examples 1 to 5. Under the irradiation of a UV lamp with a light-curing power of 25 $mW/cm^2$, the curing gelation time and gelation rate of a hydrogel liquid are tested. 0.5 ml of a homogeneous solution is loaded onto a fixture; time scan is performed at a frequency of 1 Hz with a strain of 1%; and the UV lamp is turned on at 50 s for continuously irradiating for 300 s. From the rheological data in FIG. 6(*b*), the GM/CMC/HA-Glu/Col hydrogel solutions of Examples 1 to 5 are all gelled completely at 190 s. With change of the ratio of HA-Glu to Col, the gelation time of the solutions does not change significantly, so the light-curing ability of the hydrogel is not affected by the change of the HA-Glu/Col ratio. With the increase of the HA-Glu content, the modulus of the hydrogel after curing also increases, and the cured hydrogel is harder (consistent with the analysis result of mechanical property characterization).

Cytotoxicity characterization: the biocompatibility of the material is verified by cell growth experiments, and the activity of cells in a material leaching solution is evaluated using a CCK-8 reagent. Firstly, mouse NE-4C neural stem cells are seeded into a 96-well plate at a density of 3,000 cells per well, and cultured in complete medium (100 μl/well) for 24 h. Then 3 groups (a positive control group, a blank control group and an experimental group) are designed. The blank control group is continued to be cultured with the complete medium; the positive control group is incubated with a 0.65% phenol solution; and the experimental group is cultured with the GM/CMC/1HA-Glu/7Col, GM/CMC/2HA-Glu/6Col, GM/CMC/4HA-Glu/4Col, GM/CMC/6HA-Glu/2Col and GM/CMC/7HA-Glu/1Col hydrogels of Examples 1 to 5 respectively. The above experiment is performed for 7 days, and the medium is changed once a day. A working solution is prepared from a CCK-8 stock solution and the corresponding medium in a volume ratio of 1:10 and kept in the dark for later use. The detection process is as follows: firstly, the original medium in the well plate is removed, then the CCK-8 working solution is added (110 μl/well) to the well plate, and the well plate is placed in an incubator for 2 h, and during this process, air bubbles are avoided. Finally, the absorbance at a wavelength of 450 nm of the solution to be tested is measured using a multifunctional microplate reader (Read-Max 1900, Shanghai Flash Spectrum Biotechnology Co., Ltd.) on the 7th day, and the OD value is read. 5 or more samples are tested, and the experiment is repeated for n=3 times. Then, outliers are eliminated by Dixon's test, and the data is expressed as standard deviation of the mean (SD). Finally, the relative growth rate RGR of the cells is expressed in percentage by the following equation.

$$RGR=OD_{450e}/OD_{450b}\times100\%$$

Figure 7:
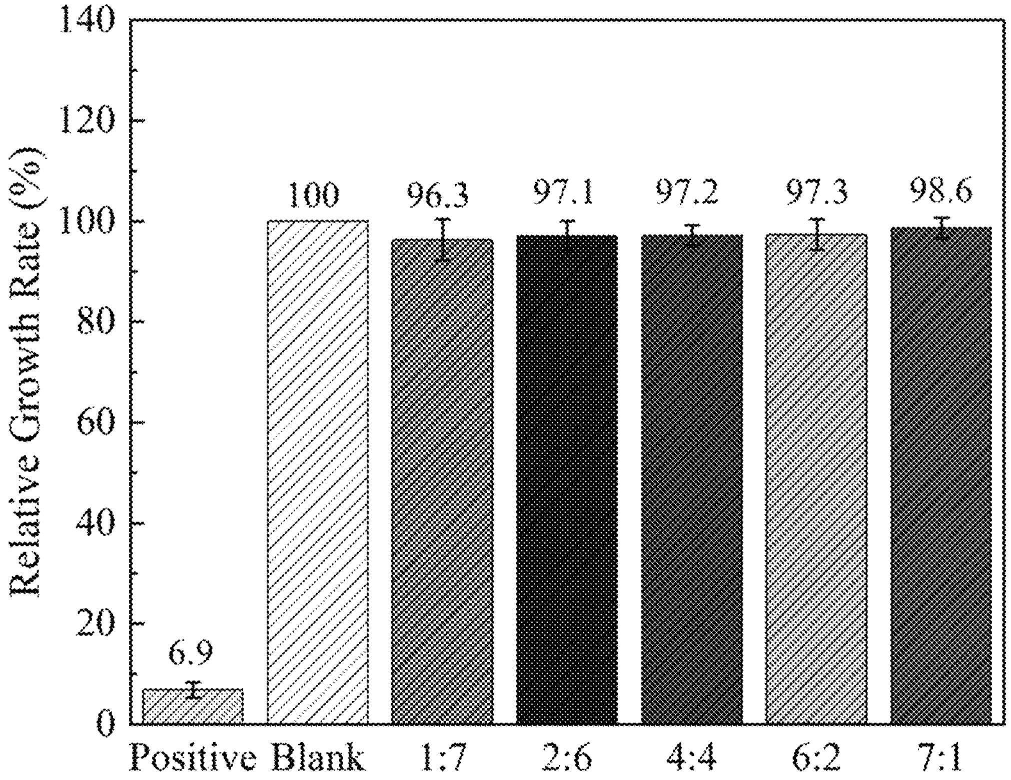
FIG. 7 shows relative growth rate RGR of cells cultured with hydrogels prepared in Examples 1 to 5 of the present disclosure.

$OD_{450e}$ is the average optical density of the sample leaching solution measured; $OD_{450b}$ is the average optical density of the blank group, and the results are shown in FIG. 7. The lower the survival rate, the higher the cytotoxic potential of the test sample, and the cytotoxicity grade is shown in Table 1.

Combining FIG. 7 and Table 1, the relative growth rate RGR and toxicity grade on the 7th day can be found. The positive control group has an RGR of only 6.9%, and a cytotoxicity grade of 4, which indicates that the sample is toxic. The experimental group has RGRs of all 90% or above, and a cytotoxicity grade of 1, which indicates that the hydrogel samples prepared in Examples 1 to 5 are non-toxic to cells. Therefore, the prepared hydrogel system has good biocompatibility and no cytotoxicity.

TABLE 1

| Test results of cytotoxicity of hydrogel materials | | | |
|---|---|---|---|
| Day | Group | RGR | Cytotoxicity grade |
| 7 | Positive control | 6.9% | 4 |
| | Blank control group | 100% | 0 |
| | 1:7 | 96.3% | 1 |
| | 2:6 | 97.1% | 1 |
| | 4:4 | 97.2% | 1 |
| | 6:2 | 97.3% | 1 |
| | 7:1 | 98.6% | 1 |

RGR <24%, grade 4, unqualified, cytotoxic
RGR >75%, grade 1, qualified, non-cytotoxic The above descriptions are merely preferred embodiments of the present disclosure and are not intended to limit the present disclosure. For a person skilled in the art, the present disclosure may have various modifications and changes. Any modification, equivalent replacement, or improvement made without departing from the spirit and principle of the present disclosure shall fall within the protection scope of the present disclosure.

What is claimed is:

1. A method for preparing a composite hydrogel, comprising:

(1) grafting L-glutamic acid containing an amino group to a molecular chain of hyaluronic acid containing a carboxyl group through a peptide bond to obtain a hyaluronic acid-glutamic acid polymer (HA-Glu); dissolving the hyaluronic acid-glutamic acid polymer (HA-Glu), type I collagen (Col) and sodium chloride in an HCl solution to form a mixed solution of the hyaluronic acid-glutamic acid polymer and the type I collagen;

(2) dissolving a photoinitiator lithium phenyl-(2,4,6-trimethylbenzoyl) pho-sphinate (LAP) in an NaCl solution and heating a resulting solution in a water bath to form an LAP solution;

(3) dissolving gelatin methacryloyl (GelMA) in the LAP solution, and heating a resulting solution in a water bath until the gelatin methacryloyl fully dissolves to form a gelatin methacryloyl solution;

(4) dissolving sodium carboxymethyl cellulose (NaCMC) in the LAP solution, and heating a resulting solution in a water bath until the sodium carboxymethyl cellulose fully dissolves to form a sodium carboxymethyl cellulose solution; and (5) mixing the HA-Glu/Col mixed solution prepared in step (1), the GelMA solution prepared in step (3) and the NaCMC solution prepared in step (4) to form a composite solution, then adding a tartrazine with light-blocking property, and performing sterile filtration with a 0.22 μm sterile filter to finally obtain the composite hydrogel.

2. The method for preparing a composite hydrogel according to claim 1, wherein in step (1), a method for preparing the hyaluronic acid-glutamic acid polymer specifically comprises: dissolving hyaluronic acid in an MES buffer at 55 °C, and then adding 1-ethyl-3-(3-dimethylaminopropyl) carbodiimide hydrochloride and N-hydroxysuccinimide to the solution for activation at 37 °C; after the activation, dissolving L-glutamic acid hydrochloride in the solution at 37 °C, and continuing to stir the solution at 37 °C for sufficient reaction.

3. The method for preparing a composite hydrogel according to claim 1, wherein in step (1), the type I collagen is dissolved in the HCl solution at 4 °C, then sodium chloride is added, the solution is heated to 37 °C, and the hyaluronic acid-glutamic acid polymer is added to the solution and stirred to fully dissolve; the pH is adjusted with 0.1 M NaOH at 37 °C to finally obtain the mixed solution of the hyaluronic acid-glutamic acid polymer and the collagen.

4. The method for preparing a composite hydrogel according to claim 1, wherein in step (2), a mass volume concentration of LAP in the LAP solution is 0.25%; and in step (2), heating is performed in the water bath at 60 °C for 30 min.

5. The method for preparing a composite hydrogel according to claim 1, wherein in step (3), a mass volume concentration of the gelatin methacryloyl solution is 14%; and in step (3), heating is performed in the water bath at 60 °C.

6. The method for preparing a composite hydrogel according to claim 1, wherein in step (4), a mass volume concentration of the sodium carboxymethyl cellulose solution is 1.9%; and in step (4), heating is performed in the water bath at 60 °C.

7. The method for preparing a composite hydrogel according to claim 1, wherein in step (5), a volume fraction of the gelatin methacryloyl solution in the composite solution is 42%; in step (5), a volume fraction of the sodium carboxymethyl cellulose solution in the composite solution is 16%; in step (5), a volume fraction of the mixed solution of the hyaluronic acid-glutamic acid polymer and the type I collagen in the composite solution is 42%; and in step (5), a mass volume concentration of the tartrazine with light-blocking property in the composite solution is 0.05%.

8. The method for preparing a composite hydrogel according to claim 1, further comprising: in a sterile environment, uniformly mixing the composite hydrogel obtained in step (5) with mouse NE-4C neural stem cells, and then performing light-cured 3D printing under 405-nm ultraviolet light to obtain the composite hydrogel scaffold.

* * * * *